US005869539A

United States Patent [19]
Garfield et al.

[11] Patent Number: 5,869,539
[45] Date of Patent: Feb. 9, 1999

[54] EMULSIONS OF PERFLUORO COMPOUNDS AS SOLVENTS FOR NITRIC OXIDE (NO)

[75] Inventors: R. E. Garfield, Friendswood, Tex.; A. T. Balaban, Bucharest, Romania; W. A. Seitz, Dickinson, Tex.

[73] Assignees: Board of Regents, The University of Texas System, Austin; The Texas A&M University System, College Station, both of Tex.

[21] Appl. No.: 633,337

[22] Filed: Apr. 17, 1996

[51] Int. Cl.$^6$ ..................................................... A01N 29/02
[52] U.S. Cl. .......................... 514/746; 514/743; 514/759; 514/832; 514/833; 424/718; 424/673
[58] Field of Search ..................................... 514/743, 746, 514/759, 832, 833; 424/718, 673

[56] References Cited

U.S. PATENT DOCUMENTS 5,498,421  3/1996  Grinstaff et al. .......................... 424/450

FOREIGN PATENT DOCUMENTS

WO 96/40058  12/1996  WIPO .

OTHER PUBLICATIONS

Abdalla, Hossam I., MD, ChB, et al., "Prevention of Bone Mineral Loss is Postmenopausal Women by Norethisterone", *Obstetrics and Gynecology*, vol. 66, No. 6, pp. 789–792, Dec. 1985.

Ahokas, Robert A., et al., "Enhanced Endothelium–Derived Relaxing Factor Activity in Pregnant Spontaneously Hypertensive Rats", *Suppl to Am J Obstet Gynecol*, Part 2, vol. 164, No. 1, p. 242, 1991.

Alam, A.S.M. Towhidul, et al., "A Hypothesis for the Local Control of Osteoclast Function by $Ca^{2+}$, Nitric Oxide and Free Radicals", *Bioscience Reports*, vol. 12, No. 5, pp. 369–380, 1992.

Bredt, David S. and Snyder, Soloman H., "Isolation of nitric oxide synthetase, a calmodulin–requiring enzyme", *Proc. Natl. Acad. Sci. USA*, vol. 87, pp. 682–685, Jan. 1990.

Clark, Jr., Leland C. and Gollan, Frank, "Survival of Mammals Breathing Organic Liquid Equilibriated with Oxygen at Atmospheric Pressure", *Science*, vol. 152, pp. 1755–1756, Jun. 24, 1966.

Clark, Jr., Leland C. and Shaw, Robert F., "Stable emulsions of highly fluorinated organic compounds for preparation of artificial blood formulations", *Chemical Abstracts*, vol. 107:242588t, 1987.

Erner, William E., "Preparation of fluorinated triethylenediamines for an oxygen transport agent and blood–substitute emulsion containing them", *Chemical Abstracts*, vol. 113:138569a, No. 16, 1990.

Furchgott, Robert F. and Zawadzki, John V., "The obligatory role of endothelial cells in the relaxation of arterial smooth muscle by acetylcholine", *Nature*, vol. 288, pp. 373–376, Nov. 1980.

Geyer, Robert P., Ph.D., "Fluorocarbon–Polyol Artificial Blood Substitutes", *Seminars in Medicine of the Beth Israel Hospital Boston*, vol. 289, No. 20, pp. 1077–1082, Nov. 15, 1973.

Ignarro, Louis J., "Signal Transduction Mechanisms Involving Nitric Oxide", *Biochemical Pharmacology*, vol. 41, No. 4, pp. 485–490, 1991.

Izumi, Hidetaka, MD, PhD, et al., "Gestational changes in L–arginine–induced relaxation of pregnant rat and human myometrial smooth muscle", *Am J. Obstet Gynecol*, vol. 169, No. 5, pp. 1327–1337, Nov. 1993.

Kasten, Thomas P., et al., "Potentiation of osteoclast bone–resorption activity by inhibition of nitric oxide synthase", *Proc. Natl. Acad. Sci. USA*, vol. 91, pp. 3569–3573, Apr. 1994.

Kaufman, Robert J. and Richard, Thomas J., "Emulsions of highly fluorinated organic compounds as blood substitutes", *Chemical Abstracts*, vol. 113:46356a, 1990.

Lees, Christoph, et al., "Arrest of preterm labour and prolongation of gestation with glyceryl tinitrate, a nitric oxide donor", *The Lancet*, vol. 343, pp. 1325–1326, May 28, 1994.

Lowik, Clemens W.G.M., et al. "Inducible Production Nitric Oxide in Osteoblast–like Cells and in Fetal Mouse Bone Explants Is Associated with Suppression of Osteoclastic Bone Resorption", *J. Clin. Invest.*, vol. 93, pp. 1465–1472, Apr. 1994.

MacIntyre, Iain, et al., "Osteoclastic inhibition: An action of nitric oxide not mediated by cyclic GMP", *Proc. Natl. Acad. Sci. USA*, vol. 88, pp. 2936–2940, Apr. 1991.

Molnar, Miklos, MD, and Hertelendy, Frank, PhD, DSc, "Nω–Nitro–L–arginine, an inhibitor of nitric oxide synthesis, increases blood pressure in rats and reverses the pregnancy–induced refractoriness to vasopressor agents", *Am J. Obstet Gynecol*, vol. 166, No. 5, pp. 1560–1567, May 1992.

Moncada, S., et al., "Nitric Oxide: Physiology, Pathophysiology, and Pharmacology", *Pharmacological Reviews*, vol. 43, No. 2, pp. 109–172, Feb. 1991.

(List continued on next page.)

*Primary Examiner*—Marianne M. Cintins
*Assistant Examiner*—Dwayne C. Jones
*Attorney, Agent, or Firm*—Arnold, White & Durkee

[57] ABSTRACT

The present invention involves perfluoro compound emulsions including nitric oxide, their preparation and their use. These emulsions provide a new source of nitric oxide. Such nitric oxide-containing emulsions may be used for the administration of nitric oxide to individuals in need thereof. Individuals in need of nitric oxide administration can include those suffering from hypertension, preeclampsia and a number of other situations where an increased blood flow, for example, is desirable. In addition, given the long use of perfluoro compound emulsions as blood substitutes, the present invention provides a relatively safe mode for administering and distributing nitric oxide-without potential negative side effects such as toxicities due to drug metabolites.

10 Claims, 4 Drawing Sheets

OTHER PUBLICATIONS

Pinto, Aldo, PhD, et al., "Endothelial–derived relaxing factor released by endothelial cells of human umbilical vessels and its impairment in pregnancy–induced hypertension", *Am J. Obstet Gynecol*, vol. 164, No. 2, pp. 507–513, Feb. 1991.

Riess, Jean G. and LeBlanc, Maurice, "Preparation of perfluorochemical emulsions for biomedical use: principles, materials and methods", *Blood Substitutes*, Ch. 5, pp. 94–129, 1988.

Riess, Jean G. and LeBlanc, Maurice, "Solubility and Transport Phenomena in Perfluorochemicals Relevant to Blood Substitution and Other Biomedical Applications", *Pure & Appl. Chem.*, vol. 54, No. 12, pp. 2383–2406, 1982.

Riess, Jean G., "Highly fluorinated systems for oxygen transport, diagnosis and drug delivery", *Colloids and Surfaces A: Physiochemical and Engineering Aspects*, 84:33–48, 1994.

Riess, J. G., "The Design and Development of Improved Fluorocarbon–Based Products for Use in Medicine and Biology", *Art. Cells, Blood Subs., and Immob. Biotech.*, 22(2), pp. 215–234, 1994.

Roberts, James M., MD, et al., "Preeclampsia: An endothelial cells disorder", *Am J. Obstet Gynecol*, vol. 161, No. 5, pp. 1200–1204, Nov. 1989.

Schweighardt, Frank Kenneth and Kayhart, Charles Randall, European Patent Application No. EP 282,949, filed on Sep. 21, 1988, with U.S. Patent Application No. 28,521, filed on Mar. 20, 1987, *Chem. Abstr.*, 110:199223 and 199180, 1989.

Sloviter, Henry A. and Kamimoto, Toshiharu, "Erythrocyte Substitute for Perfusion of Brain", *Nature*, vol. 216, pp. 458–460, Nov. 4, 1967.

Venema, Richard C., et al., "Organization of the bovine gene encoding the endothelial nitric oxide synthase", *Biochimica et Biophysica Acta*, vol. 1218, pp. 413–320, 1994.

Weiner, Carl P., et al., "Induction of calcium–dependent nitric oxide synthase by sex hormones", *Proc. Natl. Acad. Sci. USA*, vol. 91, pp. 5212–5216, May 1994.

Yallampalli, Chandrasekhar, DVM, PhD, and Garfield, Robert E., PhD, "Inhibition of nitric oxide synthesis in rats during pregnancy produces signs similar to those of preeclampsia", *Am J. Obstet Gynecol*, vol. 169, No. 5, pp. 1316–1320, Nov. 1993.

Yallampalli, Chandrasekhar, DVM, PhD, et al., "An L–arginine–intric oxide–cyclic guanosine monophosphate system exists in the uterus and inhibits contractility during pregnancy", *Am J. Obstet Gynecol*, vol. 170, No. 1, Part 1, pp. 175–185, Jan. 1994.

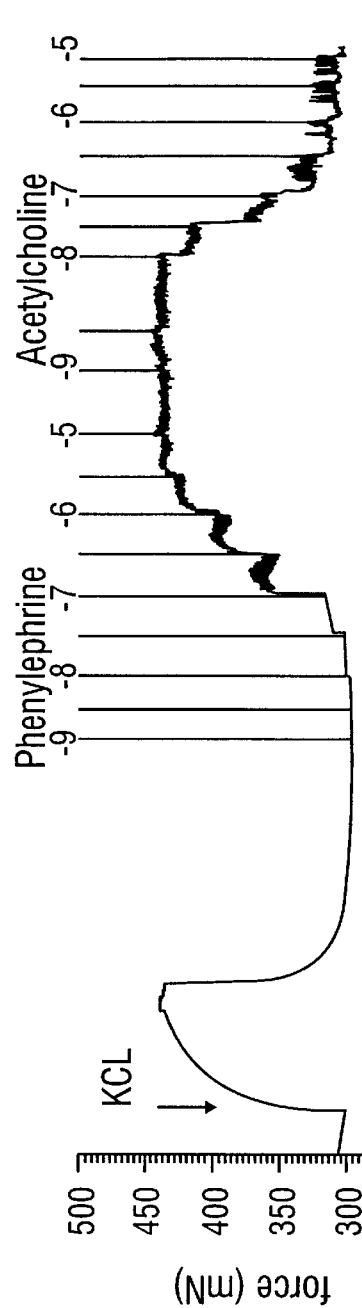
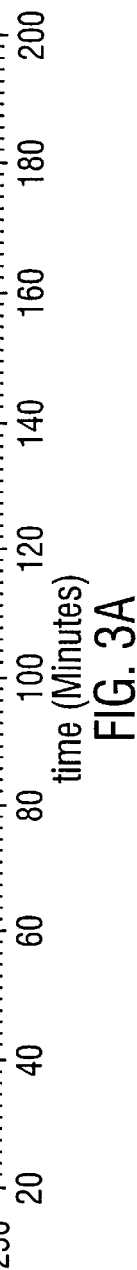
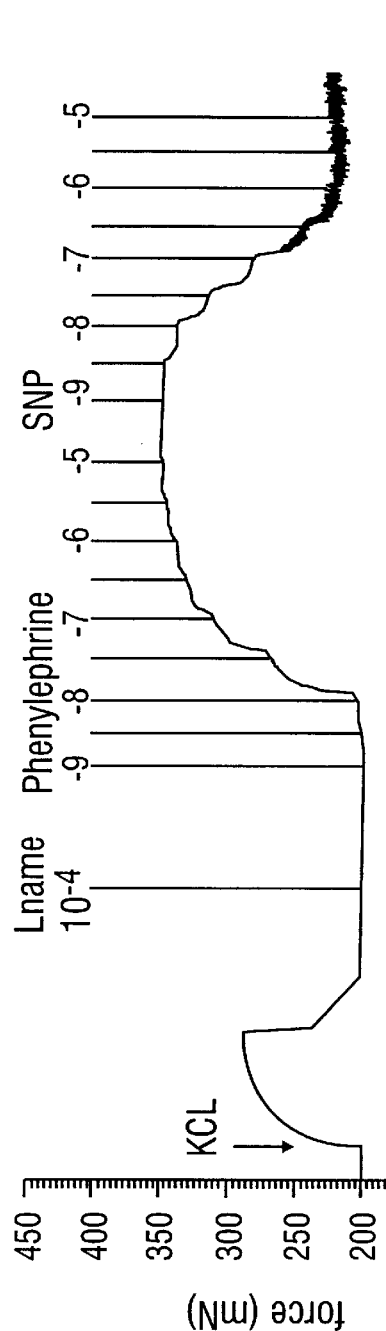
FIG. 3A
FIG. 3B

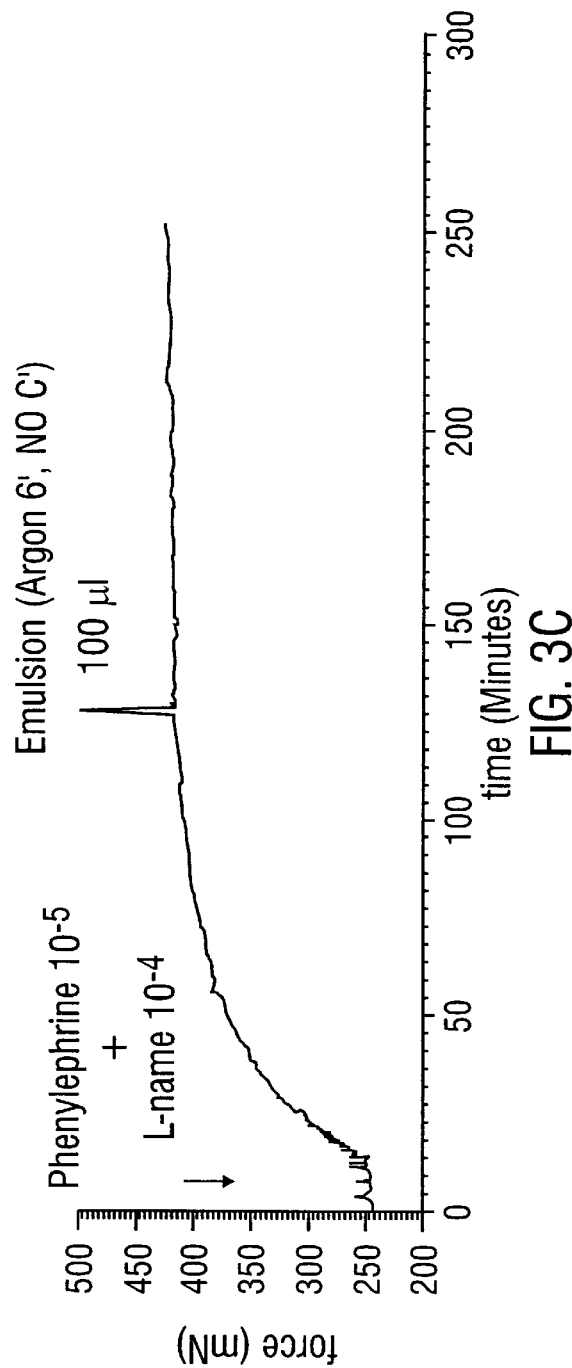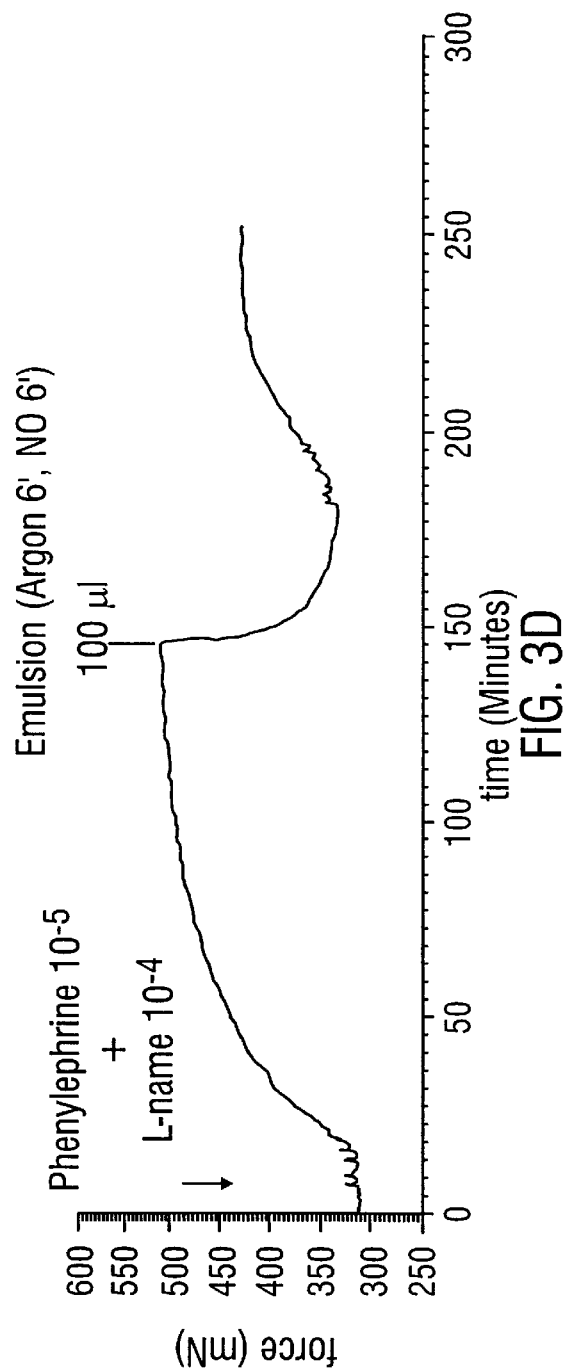

EMULSIONS OF PERFLUORO COMPOUNDS AS SOLVENTS FOR NITRIC OXIDE (NO)

FIELD OF THE INVENTION

The present invention relates to nitric oxide sources and their uses. Perfluorocarbon emulsions comprising nitric oxide and preferred nitric oxide sources.

BACKGROUND OF THE INVENTION

Furchgott and Zawadski first showed in 1980 that the endothelium must be intact for acetylcholine to produce vascular relaxation. Subsequently, numerous studies have shown that neurohumoral or pharmacological agents mediate vasodilation via the endothelium. It is now recognized that the endothelium releases a potent, labile, nonprostanoid vasodilating agent in response to various stimuli that either cause vasodilation or modulates vasoconstriction. This factor, originally termed endothelium-derived relaxing factor (EDRF), has been shown to be nitric oxide (NO) or a compound with a nitric oxide moiety.

NO is synthesized by the oxidative deamination of a guanidino nitrogen of L-arginine by at least three different isoforms of a flavin-containing enzyme, nitric oxide synthase (Moncada et al., 1991). Nitric oxide synthase has been recently purified and their genes cloned (Bredt and Snyder, 1990; Stuehr et al., 1991). Synthesis of nitric oxide has been shown to be competitively inhibited by analogues of L-arginine; N $^G$-nitro-L-arginine methyl ester (L-NAME), N$^G$-monoethyl-L-arginine (L-NMMA), N-iminoethyl-L-arnithine (L-NIO), L-monomethyl-L-arginine (L-NNMA) and L-N$^G$-methylarginine (L-NMA), and Nw-nitro-L-arginine (L-NA).

NO is an ideal local transcellular messenger because of its small size, lipophilic nature, and short duration of action. Commonly used chemical nitro-vasodilators, such as nitroglycerin and nitroprusside, appear to act by releasing NO.

Nitric oxide synthases (NOs) are enzymes that synthesize NO from arginine. These enzymes have been cloned and characterized since they were first described in 1989. Three distinct isoforms have been purified, cloned and expressed, and there is evidence for the presence of NOS in almost every tissue of the mammalian body, albeit at widely different levels. The isoforms include bNOS (brain NOS), eNOS (epithelial NOS), and mNOS (macrophage NOS ir iNOS—inducible NOS). The bNOS and eNOS isoforms are constitutive and stimulated by calcium. The iNOS form is expressed in response to a variety of cytokines. Their roles are briefly outlined below.

| bNOS<br>Nervous System | eNOS<br>Cardiovascular System | iNOS<br>Non-specific Immunity |
| --- | --- | --- |
| CNS neurotrans-<br>mitter/neuromodulator:<br>• responses to<br>glutamate<br>• synaptic plasticity?<br>• nociception | Relaxation of vascular<br>smooth muscle:<br>• regulation of tissue<br>conductance<br>• regulation of blood<br>flow<br>• regulation of blood<br>pressure | Resistance to:<br>• bacteria<br>• fungi<br>• protozoa<br>• tumours? |
| Likely Pathological roles<br>include ischaemic brain<br>damage epilepsy? | Inhibition of platelet<br>aggregation and<br>reactivity | Pathological roles:<br>Shock states caused<br>by: endotoxin/sepsis<br>• cytokines |
| Peripheral<br>nonadrenergic,<br>noncholinergic<br>(NANC) nerve<br>transmitter:<br>• GI tract<br>• penile erection<br>• bladder sphicter<br>• blood flow | | Inflammatory and<br>autoimmune disease:<br>• acute inflammation<br>• ulcerative colitis<br>• transplant rejection<br>• arthritis?<br>• multiple sclerosis<br>• asthma? |

Nitric oxide elevates levels of cGMP (1,3,5-cyclic guanosine monophosphate) within vascular smooth muscle to produce relaxation and reduce the tone of blood vessels (Moncada et al., 1991). Nitric oxide binds to heme and thus activates soluble guanylate cyclase (Ignarro, 1991) to increase cellular content to cGMP. It has long been recognized that nitrovasodilators, such as nitroprusside and nitroglycerin, inhibit vascular smooth muscle contractility to produce relaxation or reduce vascular tone. These agents have been used since the late 1800's as vasodilators. However, it has only been recently that the mechanism of action of these compounds has been realized. Nitrovasodilators are now classified as nitric oxide sources (Moncada et al., 1991). The long-used nitrovasodilators may be regarded as substitution therapy for a failing physiological mechanism. Nitric oxide is also produced by macrophages and other immune cells (Stuehr et al., 1991). Stimulated macrophages produce nitric oxide from L-arginine and it is considered the first line of defense against invading pathogens.

There is a substantial body of evidence from animal studies that a deficiency in nitric oxide contributes to the pathogenesis of a number of diseases, including hypertension, atherosclerosis and diabetes (Moncada et al., 1991). There are many recent studies showing that inhibition of nitric oxide synthase dramatically increases blood pressure. Inhibition of nitric oxide synthesis with L-NNMA, L-NA or L-NAME cause long-lasting elevation in blood pressure and suggest that a reduction in the synthesis of nitric oxide may contribute to the pathogenesis of hypertension (Moncada et al., 1991). Furthermore, L-NAME-treatment potentiates pressor responses to angiotensin II, vasopressin and norepinephrine. Also, in patients with pregnancy-induced hypertension, release of nitric oxide by umbilical vessels is blunted (Pinto et al., 1991) and the physiological decrease in blood pressure in pregnant spontaneous hypertensive rats was shown to depend on endothelial nitric oxide (Ahokas et al., 1991). Additionally, infusion of L-NA increases blood pressure in pregnant rats and potentiates responses to vasopressors (Molnar and Hertelendy, 1992). These studies suggest that impaired nitric oxide synthesis may be an important mechanism in the etiology of pregnancy-induced hypertension (preeclampsia). Indeed inhibition of NO in pregnant rats produces symptoms identical to preeclampsia (Yallampalli and Garfield, 1993). It has been suggested that preeclampsia is an endothelial cell disorder (Roberts et al., 1989). It is possible that nitric oxide (either an over abundance or deficiency) is involved in many other pathological problems in women such as preterm labor, climaterium, pregnancy-induced diabetes, postpartum hemorrhage, coronary artery disease, cancer and behavioral and digestive problems. Nitric oxide is produced by the uterine wall and it effectively inhibits uterine contractility during pregnancy but not during delivery (Yallampalli et al., 1993b). On the other hand the steroid hormones seem to regulate the nitric oxide-cGMP relaxation mechanism in the uterus (Yallampalli et al., 1993b). It is plausible that high levels of steroid hormones (mainly progesterone) during pregnancy modulate either the production of action of nitric oxide. If nitric oxide is a transduction mechanism of steroid hormones perhaps nitric oxide regulates other estrogen— and/or progesterone—dependent steps in reproduction and women's health including ovulation, implantation, menstruation, climacterium, etc. In addition, maybe some of the actions of the antihormones (i.e., antiprogestins) are mediated through nitric oxide.

Nitric oxide is also very much involved in the control of blood clotting. Nitric oxide is a very potent inhibitor of coagulation and this action may be extremely important in preventing clotting in the placenta circulation. Previously, it has been suggested that prostacyclin regulates placental clotting. However, it is now obvious that nitric oxide may be very important in this process either in conjunction with the inhibitory effects of prostacyclin or acting alone. Nitric oxide has been found to be synthesized in almost all tissues of the body including brain, peripheral nervous systems, smooth muscle (vascular, see above), kidney, lung, uterus, etc. In the uterus nitric oxide is produced by various tissues and it is a very powerful inhibitory agent for uterine contractility (see below).

Nitric oxide modulates various biological phenomena including regulation of smooth muscle contractility of several tissues. Nitric oxide is synthesized from L-arginine and causes relaxation of smooth muscle by elevating cyclic guanosine monophosphate (cGMP)—levels. In the inventors' studies, rat uterine tissues in vitro were examined to determine whether an L-arginine-nitric oxide-cGMP system is present in the rat uterus (Garfield and Yallampalli, 1993; Yallampalli et al., 1993b; Izumi et al., 1993). These studies show that (1) the substrate and a donor of nitric oxide produced uterine relaxation, (2) inhibitors of the nitric oxide—cGMP pathway blocked the relaxation responses, (3) nitric oxide synthase was localized to several uterine cell types, (4) nitric oxide was produced by the uterus during periods when L-arginine was consumed and citrulline levels increased, (5) effects of nitric oxide substrate on relaxation were mimicked by cGMP, (6) the responses to L-arginine and NO were decreased during term and preterm labor, (7) the NOS isoforms are present in the uterus and up-regulated during pregnancy but decreased when labor begins. These studies indicate that NO may control uterine contractility during pregnancy.

Based upon the above considerations nitric oxide donors should be potential uterine relaxants and nitric oxide inhibitors may increase uterine contractility. Recent data support these contentions. The nitric oxide donor compound nitroglycerin has been shown to inhibit preterm labor in 13 human subjects (Lees et al., 1994). On the other hand, nitric oxide inhibition substantially improves the action of antiprogesterone compounds to induce premature birth in rats and the same compounds alone induce premature birth in guinea pigs.

During normal parturition the cervix softens or ripens and effaces to allow the fetus to descend through the birth canal. The cervix is composed mostly of connective tissue and there is a decrease in the content of this tissue during birth. The exact mechanisms responsible for initiating changes in the cervix associated with birth are unknown. However, it is well known that this process is similar to an inflammatory response and accompanied by an infiltration of white blood cells and release of enzymes (Chwalisz, 1993).

Progesterone is thought to inhibit cervical ripening and antiprogesterone compounds promote early softening and premature labor/birth. The cytokines have also been implicated in these responses (Chwalisz et al., 1994a; Chwalisz et al., 1994b).

Data from the inventors' labs suggest that nitric oxide may regulate cervical function at the end of pregnancy. The rat cervix produces nitric oxide and contains isoforms for bNOS and mNOS as judged by assays for nitric oxide and NOS using Western blots and PCR™. During labor NOS isoforms are increased and this is accompanied by an increase in NO production. Thus, NO may be involved in cervical dilatation associated with labor and delivery. This is contrary to the down-regulation of the NO pathway seen in uterus during labor and delivery (see above).

There are a number of studies that provide circumstantial evidence for the concept that the steroid hormones might modulate the NOS enzymes, guanylate cyclase and/or the effector system for cGMP. Thus, it is possible that nitric oxide synthesis, guanylate cyclase or the nitric oxide effector system (cGMP-dependent relaxation mechanism) is regulated by steroid hormones. There is an increase in cardiovascular diseases in women following menopause and these might be related to the decrease in sex steroids and an alteration in nitric oxide (see above). Female steroid hormones have been shown to modulate endothelium-dependent relaxation of vascular smooth muscle by nitric oxide. Estradiol treatment of rats is thought to cause increased nitric oxide production by vascular tissues, whereas progesterone counteracts this phenomenon (Miller and Van Houtte, 1991). On the other hand, the steroid hormones seem to regulate the nitric oxide-cGMP relaxation mechanism in the uterus (Yallampalli et al., 1993b). In addition a progesterone agonist decreased blood pressure in SHR rats and rats treated with nitric oxide inhibitor.

One important observation in regard to the above hypothesis concerning steroid hormone control of nitric oxide, is that in pregnant spontaneous hypertensive rats blood pressure declines during pregnancy (Ahokas et al, 1991). This study demonstrates that pregnancy has profound antihypertensive effect. It is well known that pregnancy is associated with an increase of cardiac output and a decrease in the resistance of virtually all the vascular beds in the body but the mechanism of this phenomenon is not known. High levels of steroid hormones (mainly progesterone) during pregnancy modulate either the production or action of nitric oxide. If nitric oxide is a transduction mechanism of steroid hormones perhaps nitric oxide regulates other hormone dependent steps in reproduction and women's health.

Recently the bovine endothelial NOS gene has been isolated and cloned (Venema et al., 1994). This study demonstrates that the 5'—flanking region contains 15 estrogen half-palindromic regions. It is conceivable that one or more of these estrogen motifs in the NOS promoter may confer estrogen responsiveness to the gene, at least in certain endothelial phenotypes. Estrogen responsiveness has been shown to increase NOS activity in the brain (Weiner et al., 1994).

All three NOS isoform genes have been shown to contain the putative AP-1 consensus sequences, therefore, the regulation of the oncogenes c-fos and c-jun in uterine tissues is a mechanism by which steroid hormones can increase NOS expression. Estrogen stimulates c-fos, jun-B and jun-D expression and decreases c-jun expression in endometrium. In contrast, estrogen stimulates c-jun in myometrium. These oncogenes regulate gene expression by binding as homo- or heterodimers to the AP-1 transcription factor site. Estrogen will increase Jun-B/c-fos and Jun-D/c-fos and c-fos/c-fos dimers in the endometrium but only c-jun/c-fos dimers in myometrium. Different dimer formation has been suggested as a mechanism for selective stimulation of gene expression through the AP-1 site mechanism. Thus the inventors suggest that NOS expression may be regulated by an AP-1 transcription factor mediated mechanism by the steroid hormones.

Premenopausal women have a lower incidence of cardiovascular disease than men. After menopause the incidence of cardiovascular disease increases progressively. The risk of coronary heart disease rapidly increases after cessation of ovarian function. These changes are thought to be hormonally mediated and related to the decrease in production of both estrogen and progesterone. Since (1) nitric oxide is very important in control of vascular function, (2) a decrease in nitric oxide production or action is related to the pathophysiological changes in blood vessels, i.e., cardiovascular disease associated with hypertension and atherosclerosis, and (3) the steroid hormones regulate nitric oxide synthesis, nitric oxide may mediate all, or at least some, of the actions of the steroid hormones to prevent cardiovascular disease in premenopausal women. It may be possible, therefore, to administer an NO donor to prevent cardiovascular disease as part of HRT (hormone replacement therapy) and bypass the adverse effects of the steroid hormones.

In addition to the above, nitric oxide has been implicated in bone remodeling (see below). Since the steroid hormones are also used to prevent osteoporosis in postmenopausal women, nitric oxide donors may prevent osteoporosis and again be indicated in HRT.

Bone-remodeling disorders such as osteoporosis and osteoarthritis are frequently associated with perturbations in the interactions between local and systemic bone-remodeling regulatory pathways. Postmenopausal bone loss associated with diminished steroid hormones is correlated with increased levels of cytokines. In addition both estrogen and progestins are effective in preventing postmenopausal bone loss (Abdalla et al., 1985; Christiansen et al., 1980).

Bone-degrading osteoclasts arise from cells within the monocyte macrophage lineage. Excessive osteoclast activity leads to high levels of bone destruction and osteoporosis. Although these cells have the unique ability to resorb bone they share various characteristics with macrophages. Macrophages release nitric oxide in response to inflammatory cytokines and agents.

A number of recent studies suggest that osteoclasts, like macrophages, synthesize nitric oxide (Kasten et al., 1994; Lowik et al., 1994; MacIntyre et al., 1991; Zaidi et al., 1993; Alam et al., 1992). In models of osteoporosis nitric oxide inhibition potentiated the loss of bone mineral density (Kasten et a/., 1994). These studies show that inhibition of NOS activity in vitro and in vivo resulted in an apparent potentiation of osteoclast activity. Nitric oxide, on the other hand, strongly suppressed osteoclast activity and bone resorption. This is thought to be independent of cGMP. This is an important distinction from NO action on smooth muscle because progesterone may control this step (see above). There are also studies which demonstrate that nitric oxide is produced by chondrocytes. It is suggested that NO production by osteogenic cells (osteoblasts and chondrocytes) represents an important regulatory mechanism of osteoclastic activity.

The possible therapeutic consequences of the above findings are tremendous. Since inhibition of osteoclastic activity is a major aim in osteoporosis, Paget bone disease and rheumatoid arthritis NO donors might be useful in these conditions. The exact relationship between nitric oxide, osteoclast activity and steroid hormones remain to be established. However, it seems likely that the steroid hormones may regulate NO synthesis in the osteoclasts and this affects their activity.

The existing data strongly indicates that the effects of chronic steroid (estrogen and/or progesterone) on blood vessels are mediated by nitric oxide. Inhibition of nitric oxide synthesis produces both atherosclerosis and osteoporosis in animal models (Moncada et al., 1991). On the other hand, nitric oxide exhibits no direct effects on the endometrium in terms of proliferation and differentiation. Therefore, it should be possible to replace steroids for HRT with a suitable nitric oxide donor. With this innovative strategy the major problems of HRT: endometrial hyperlasia and uterine bleeding can be avoided. Therefore, NO donors may be used to prevent atherosclerosis and bone loss without inducing bleeding, (so called "no blood sector in HRT"). In addition, a suitable nitric oxide donor can be used for HRT, since these compounds do not exert hormone activities.

Presently, there are only three nitric oxide donor compounds that are used clinically. These are nitroglycerin, amyl nitrite and sodium nitroprusside. Nitroglycerin is available in table for sublingual use, IV or patch forms. Amyl nitrite is formulated as an inhalant and is usually used in breakable capsules. Sodium nitroprusside is used for IV infusion only. Presently nitric oxide donors are used for angina pectoris due to coronary artery disease (nitroglycerin or amyl nitrite) and control of blood pressure associated with myocardial infraction or surgical procedures (nitroglycerin or sodium nitroprusside).

Problems with Present Nitric Oxide Donors

Problems with present nitric oxide donor compounds include the following:

1. Short duration of action
2. Short half-life
3. Lack of tissue specificity
4. Development of tolerance
5. Accumulation of toxic substances—e g, cyanide for sodium nitroprusside Nitric oxide (NO) is a gas with low solubility in water and aqueous solutions such as serum. Although NO is a free radical, it is stable and does not interact chemically with biological fluids or usual organic solvents; the situation is similar to that of oxygen, which is a stable diradical. The three gases, nitrogen, oxygen, and nitric oxide, have diatomic molecules and similar molecular weights. The first two, however, are non-polar molecules, and therefore have slightly lower solubilities in water than NO. These solubilities at 0° C. and atmospheric pressure (in grams per 100 mL water) arc 2.33, 4.89 , and 7.34 , respectively; at 20° C. and the same pressure (in mL per 100 mL water) are 1.6, 3.0 , and 4.6 , respectively. The volatilities of these three gases are also fairly similar, but again the polarity of the NO molecule makes it the least volatile, as seen from the boiling points at normal pressure: −195.8°, −183.0°, and −151.8° C.

Nitric oxide reacts instantaneously with oxygen from air, yielding nitrogen dioxide, a toxic red-brown gas. Therefore, all studies with NO must be carried out in the absence of oxygen or oxidizing media.

Perfluoro compounds (PFCs) have all their hydrogen atoms replaced by fluorine atoms. For blood substitutes, representative PFCs used in practice are perfluorinated hydrocarbons (e.g., perfluorinated decalin, perfluorinated adamantane), halogen derivatives (e.g., octyl bromide), tertiary amines (e.g., perfluorinated tributylamine or perfluorinated tripropylamine), nitrogen-containing heterocycles (e.g., perfluorinated N-methyl-isoquinoline, perfluorinated N-(4-methylcyclohexyl)-piperidine) and oxygen-containing heterocycles (e.g., perfluorinated 2-n-butyl-tetrahydrofuran). In addition, highly fluorinated atoms have also been used; examples are perfluorooctyl-ethane, perfluorohexyl-ethane, 1,2-bis(perfluorobutyl)-ethene and 1,2-bis(perfluorohexyl)-ethene. For simplicity, all these compounds will be henceforth designated as PFCs.

Clark and Golan (1966) discovered that PFCs (in particular perfluoro-2-butyl-tetrahydrofuran) are excellent solvents for gases, and this property led to using such compounds as "blood substitutes". Other historically important advances are due to Sloviter et al. who were the first to use PFC emulsions, and to Geyer who showed that "bloodless rats" (whose red blood cells had been replaced by PFC emulsions) behaved normally, and their plasma proteins and hematocrit levels returned to normal values after about one week. During the time when PFCs were the oxygen carriers instead of hemoglobin, these rats survived for two days in an atmosphere containing 20% carbon monoxide, whereas normal rats exposed to the same atmosphere died in a few minutes.

The solubility of oxygen in such PFC liquids is 35–44 mmol $O_2$/L under standard pressure and temperature, whereas water dissolves under the same conditions only 2.2 mol $O_2$/L. Such PFCs are completely inert chemically, and cause practically no adverse reactions when administered to animals or to humans.

Different types of PFCs are widely used for other medical purposes: anesthetics, orthopedic implants, replacement muscular structures, artificial heart valves, etc. In addition, it should be mentioned that (i) teflon is now manufactured in large amounts for various purposes owing to its excellent mechanical properties, chemical inertness, and self-lubricating properties; (ii) chlorofluorocarbons (CFCs) that were used for decades in spray cans, refrigerators, and air conditioners are too stable chemically and reach the stratosphere where they are broken down by the sun's hard ultraviolet radiation, destroying the ozone layer at high latitudes due to the release of chlorine atoms; these CFCs are now phased out, and are being replaced by other fluids that are less damaging to the ozone layer; hydrochlorofluorocarbons are among these replacement fluids.

Returning to PFCs, these colorless liquids with low viscosity and with densities of 1.8 to 2.0 g/mL are immiscible with water and with most organic solvents. Therefore, for intravenous administration, PFCs have to be emulsified with aqueous solutions of electrolytes and buffers, containing also surfactants and oncotic (colloid-osmotic) components. Emulsification is achieved frequently by ultrasonic vibration (sonication) followed by dialysis for removing any traces of toxic fluoride anions formed during sonication, or by high-pressure homogenization, which is more appropriate for large-scale manufacture of emulsions.

The first generation of PFCs which had been used in the late 70s for thousands of human patients in Japan, USSR, China and a few other countries, was beset by side-effects due to the instability of emulsions, to the high retention time of PFCs in the body, and to the presence of impurities formed during the synthesis of PFCs under drastic fluorination conditions. This is why in several European countries (Britain, France), and in the USA the FDA allowed the use of emulsions of PFCs only for certain therapeutic purposes involving ischaemic tissues (e.g., myocardial damage during balloon angioplasty). A representative of first-generation PFC emulsion called Fluosol was manufactured in Japan by Green Cross Corporation, and its composition is presented in Table 1. It resulted by mixing three separate solutions prior to emulsification and administration.

TABLE 1

Composition of Fluosol (a 10% emulsion in injectable water) (% w/v)

| Stem emulsion (frozen) | | |
|---|---|---|
| Perfluorodecalin | 14.0 | oxygen carrier |
| Perfluoro-tripropylamine | 6.0 | oxygen carrier |
| Pluronic F-68 | 2.7 | surfactant |
| Yolk phospholipids | 0.4 | surfactant |
| Glycerol | 0.8 | cryoprotector |
| Annex solution C | | |
| Potassium chloride | 0.034 | ionic balance |
| Sodium hydrogen carbonate | 0.210 | pH control |
| Annex solution H | | |
| Sodium chloride | 0.60 | ionic balance |
| Calcium chloride | 0.028 | osmotic pressure control |
| Magnesium chloride | 0.020 | osmotic pressure control |
| Glucose | 0.180 | nutrient |
| Hydroxyethyl-starch | 3.0 | oncotic agent |

The Pluronic F-68 surfactant was a non-ionic block copolymer of ethylene oxide and propylene oxide; this polyoxyethylene-polyoxypropylene copolymer with an average molecular weight of 8400 gave sometimes transient acute reactions in humans (due to complement activation); this led to the necessity of a pre-screening before administering the PFC emulsion.

The present, second-generation of PFC emulsions remedied most of the drawbacks of first-generation precursors. The PFCs are prepared under milder conditions, namely by strating from pure perfluoro precursors and reacting them with another compound, yielding thus a pure substance. For the optimal trade-off between too low volatility (leading to long retention times in the body) and too high volatility (leading to pulmonary problems), the range of molecular weights of the PFCs should lie within the limits of 460–520 daltons. The optimal particle size is 0.1–0.3 $\mu$m. The surfactants used at present afford emulsions that have a long shelf-life at room temperature in the final, sterile emulsion. See, e.g., Schweighardt, Kaufman et al.; Erner; and Clark, Jr., et al. (1987).

Prior to the present invention it was not known that perfluoro compound emulsions were excellent nitric oxide solvents and usable to donate nitric oxide to biological systems.

SUMMARY OF THE INVENTION

This invention discloses an emulsion comprising a perfluoro compound and nitric oxide and uses thereof. Methods of preparing such a nitric oxide source suitable for in vivo administration are described. These comprise dissolving nitric oxide in a perfluoro compound emulsion solvent. This method is useful for treating a mammal with nitric oxide by administering an emulsion comprising a perfluoro compound and nitric oxide. Exemplary conditions benefitting from appropriate nitric oxide treatment include hypertension, angina, preeclampsia and a wide variety of additional conditions, for example, those involving unduly restricted blood flow.

The nitric oxide and perfluoro compound-containing emulsions of the present invention preferably involve a perfluorinated hydrocarbon as the perfluorinated compound, although perfluorinated heterocyclics, hydrocarbon amine or analogous types of compounds may be utilized. Preferred perfluoro compounds include: perfluorinated decalin, perfluorinated adamantane, perfluorinated tributylamine, perfluorinated tripropylamine, perfluorinated N-methylisoquinoline, perfluorinated N-(4-methylcyclohexyl)-piperidine), perfluorinated 2-n-butyl-tetrahydrofuran, perfluorooctyl-ethane, perfluorohexyl-ethane, 1,2-bis(perfluorobutyl)-ethene or 1,2-bis(perfluorohexyl)-ethene.

An important aspect of the present invention is preparing emulsions comprising a perfluoro compound and nitric oxide suitable for in vivo administration. Such administration should be in a therapeutically effective amount, i. e., that amount correcting the particular biological problem. The administration may be parenteral, topical or intracavitary. An intravascular administration may be a preferred mode of parenteral administration, for example, for treatment of hypertension. Intracavitary administration may be, for example, bronchial (by inhalation) cervical, uteral or vaginal (for remedying disorders of the reproductive tract), oral (for example, held contained in a pouch) or anal. The most widely acknowledged use of nitric oxide is to induce vascular dilation. Thus, blood pressures may be decreased and blood perfusion directed to a desired site, the latter often involving administration of the nitric oxide donor to that site or to that site's blood supply region.

BRIEF DESCRIPTION OF THE DRAWINGS

FIG. 3A–D shows contractile effects of phenylephrine, KCI, acetylcholine, sodium nitroprusside perfluorocarbon emulsion and NO-containing perfluorocarbon emulsion on mammalian aortic rings.

DETAILED DESCRIPTION OF THE INVENTION

Figure 1:
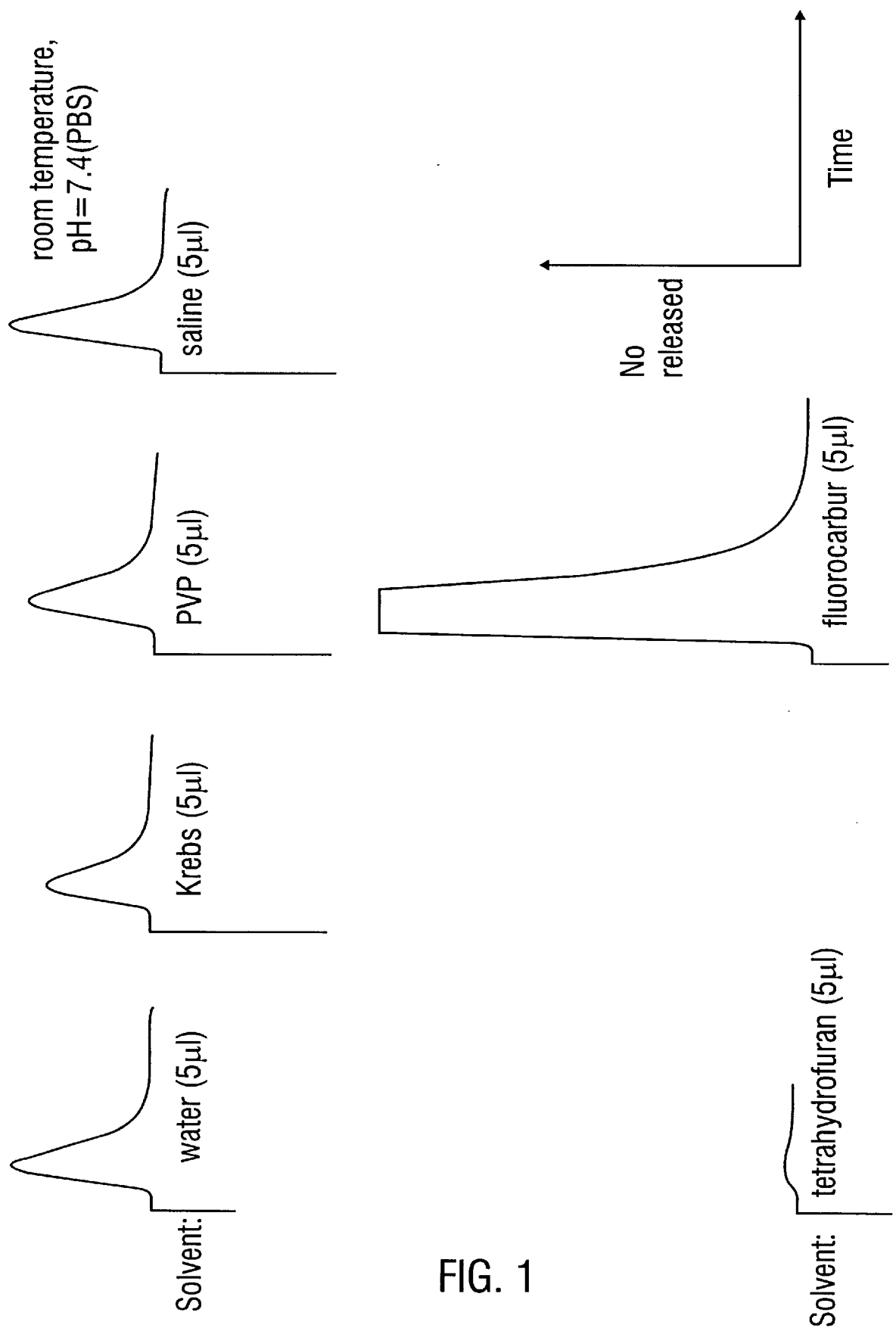
FIG. 1 presents the determination of NO concentrations by chemiluminescence in the emulsion of perfluoro compound described.

NO is very unstable in nature, readily reacting with oxygen, for example. No stabilizing solvent for NO is known and hence delivery of NO to the body must proceed via known direct or indirect nitric oxide drug donors or a substrate for the enzyme, nitric oxide synthase. Drugs such as nitroglycerin, while known to act as NO donors, do so via mechanisms which are unknown.

Indications for NO sources, where, for example, the NO-containing perfluoro compound emulsions of the present invention can be used, are as follows:

Cardiovascular includes hypertension, angina, atherosclerosis, preeclampsia (pregnancy induced hypertension, toxemia, eclampsia, HELP syndrome), regulation of vascular conductance, regulation of blood flow, regulation of blood pressure, and myocardial ischemia.

Gastrointestinal diseases to alter motility, pyloric stenosis.

Lung function including asthma, treatment of premature babies to increase lung function and pulmonary hypertension.

Inflammation, autoimmune and immune diseases and conditions including acute inflammation, arthritis, resistance to infection, cancer, SLE—Lupus, anaphylactic reactions and allograft rejection CNS, includes behavior, epilepsy, Alzheimer's disease, stroke, growth hormone disorders (e.g., acromegaly).

Pancreas includes diabetes.

Female reproductive systems or problems (direct and indirect) such as ovulation, implantation/in vitro fertilization, premenstrual syndrome, dysmenorrhea, uterine contractile disorders, premature labor, cervical dilation, contraception, menopause symptoms, osteoporosis, endocrine disorders and-hormone replacement therapy.

Male reproductive problems (direct and indirect) such as impotence, penile erection, male menopause symptoms, endocrine disorders, osteoporosis and prostate hypertrophy.

Bladder and kidney problems, including incontinence, renal arterial stenosis, hypertension, topical hair loss, various dermatological problems, eczema (skin reaction to foreign particle), autoimmune skin diseases and psoriasis.

These situations can be sorted as primary, where NO sources are usable, or secondary, where they are likely to be usable. Primary indications include uterine contractility disorders including dysmenorrhea, preterm labor and cervical incompetence; hormone replacement therapy in women and men; and hypertension treatment. Secondary (potential) indications include behavior, ovulation and implantation—contraception, induction of labor, blood clotting, impotence, infections, postpartum hemorrhage, breakthrough bleeding, topical applications, lung function and cancer.

The present invention involves a discovery that NO is soluble and stable in deoxygenated perfluoro compound emulsions. When dissolved in such perfluoro compound emulsions, NO is stable for periods of at least 14 days or longer if stored in the absence of oxygen. The data presented herein show the presence of NO in the samples after this time. Such emulsions are advantageous because of their biological compatibility (synthetic blood, see, e.g. Pries and Riess et al 1982, 1988 and 1994) as well as their NO solvent characteristics (releasing NO to afect biological tissue).

The combination of these concepts and their experimental verification is novel and unexpected. NO can be kept stable in an emulsion previously demonstrated to be suitable for injection into the human blood system (indeed these emulsions have been used in blood replacement therapy). With NO adsorbed to the perfluorocarbons (as opposed to oxygen being adsorbed in the usual application) this provides a mechanism for delivery of NO to tissues. Desired NO doses (i. e., how much NO to dissolve in a given volume of emulsion to achieve a particular biological response) may first be determined using various NO levels in, e.g, different blood substitutes and other perfluorocarbon emulsions. An important discovery is disclosed herein, namely that the inventors can keep NO substantially stable for periods of weeks in biologically compatible perfluoro compound emulsions. This has been proved experimentally, and the potential applications are enormous.

EXAMPLE 1

Solutions of Nitric Oxide in Emulsions of Perfluoro Compounds

The composition of a second-generation PFC emulsion used as a solvent for nitric oxide, is shown in Table 2. It contains a small amount of fluorocarbon-hydrocarbon "molecular dowel" compound (1-perfluoro-n-hexyl-decane) which inserts between the surface of the PFC droplet and the phospholipid surfactant. It has a much higher concentration of PFC than first-generation PFC emulsions.

TABLE 2

Perfluoro-octyl-ethane emulsion (60% w/w)

| | |
|---|---|
| Perfluoro-octyl-ethane | 60 grams |
| Egg yolk phospholipids | 4 grams |
| Dowel PFC | 2.8 grams |
| Dihydrogen sodium phosphate hydrate | 0.052 grams |
| Hydrogen disodium phosphate heptahydrate | 0.355 grams |
| D-α-Tocopherol | 0.002 grams |
| Disodium calcium EDTA dihydrate | 0.020 grams |
| Sodium chloride | 0.250 grams |
| Water (distilled, pyrogen-free, injectable) | q.s. ad 100 mL |

This perfluorocarbon emulsion was prepared by microfluidization, and sterilized at 121° C. for 15 minutes. The pH (post-sterile) adjusted by the sodium phosphate buffer was 6.9. The average particle size (measured by photo sedimentation) was 0.08 $\mu$m and 0.12 $\mu$m before and after sterilization.

Emulsions of PFCs dissolve gases by a purely physical process, and the solubility varies linearly with the partial pressure of the gas according to Henry's law. The higher the molecular weight of the gas, the higher the solubility. It can therefore be expected that the solubility of NO should be intermediate between that of $O_2$ and $N_2$.

For preparing solutions of NO in PFC emulsions, oxygen is preferably excluded and at the same time the sterility of the emulsion conserved. This is best done by means of having a vial with sterile PFC emulsion capped with a rubber septum; through syringe needles, the emulsion is then deoxygenated and NO is introduced.

Procedures that can be applied for deoxygenation include (i) repeated cycles of freezing, evacuating the gas in the vial with a vacuum pump, and thawing; or (ii) displacing dissolved oxygen by bubbling an inert gas such as nitrogen or argon; the latter is preferred because it is easily available in oxygen-free pressure cylinders, and because it provides a good, heavy gas blanket even if there is a small leak. The procedure for the second alternative is described below.

EXAMPLE 2

Preparation of NO Solutions in PFC Emulsions Using Argon Deoxygenation

The emulsion is placed in a suitable vial, which is tightly closed with a rubber septum through which two syringe needles are inserted; one of these reaches to the bottom of the vial and serves for introducing the gases, the other allows excess gas to escape into the hood where the operation is performed.

Argon gas from a pressurized cylinder is bubbled through the emulsion for 3–4 minutes, after which, with a suitable 3-way stopcock, gaseous nitric oxide (NO) is bubbled through the same syringe needle for 5 minutes. It was found advantageous to use two (instead of one or three) syringe needles for preventing the septum from allowing the contents of the vial to come in contact with the atmosphere, because as soon as nitric oxide encounters oxygen, it may be converted into nitrogen dioxide. For the small septum usually needed, three syringe needles are too crowded, and unnecessarily increase the number of holes through the septum. With a single syringe needle overly complicated stopcock systems are needed.

At the end of the operation, both syringe needles are simultaneously removed from the septum, while the stream of NO is still flowing through. The nitric oxide solution can be kept at room temperature for at least several days and, if cooled in the refrigerator (not freezer), is stable for several weeks. The concentration of NO can be measured by using standard chemiluminescent methods, particularly for nitrite or other oxidation products of NO or by other analytical procedures.

FIG. 1 presents the determination of NO concentrations by chemiluminiscence in the emulsion of perfluoro compound described in Table 2, in comparison with solutions prepared similarly in the following solvents: distilled water, 0.9% aqueous saline solution, Krebs solution, colloidal solution of poly(vinylpyrrolidone), and tetrahydrofuran. It can be seen that the concentration of NO in the PFC emulsion is one order of magnitude higher than in the other solvents, allowing such concentrated solutions to be used in small amounts for medical applications. When a low concentration of NO is acceptable, solutions of NO in other biocompatible solvents such as saline solution, Krebs solution, or colloidal poly(vinylpyrrolidone) may also be employed.

Figure 2:
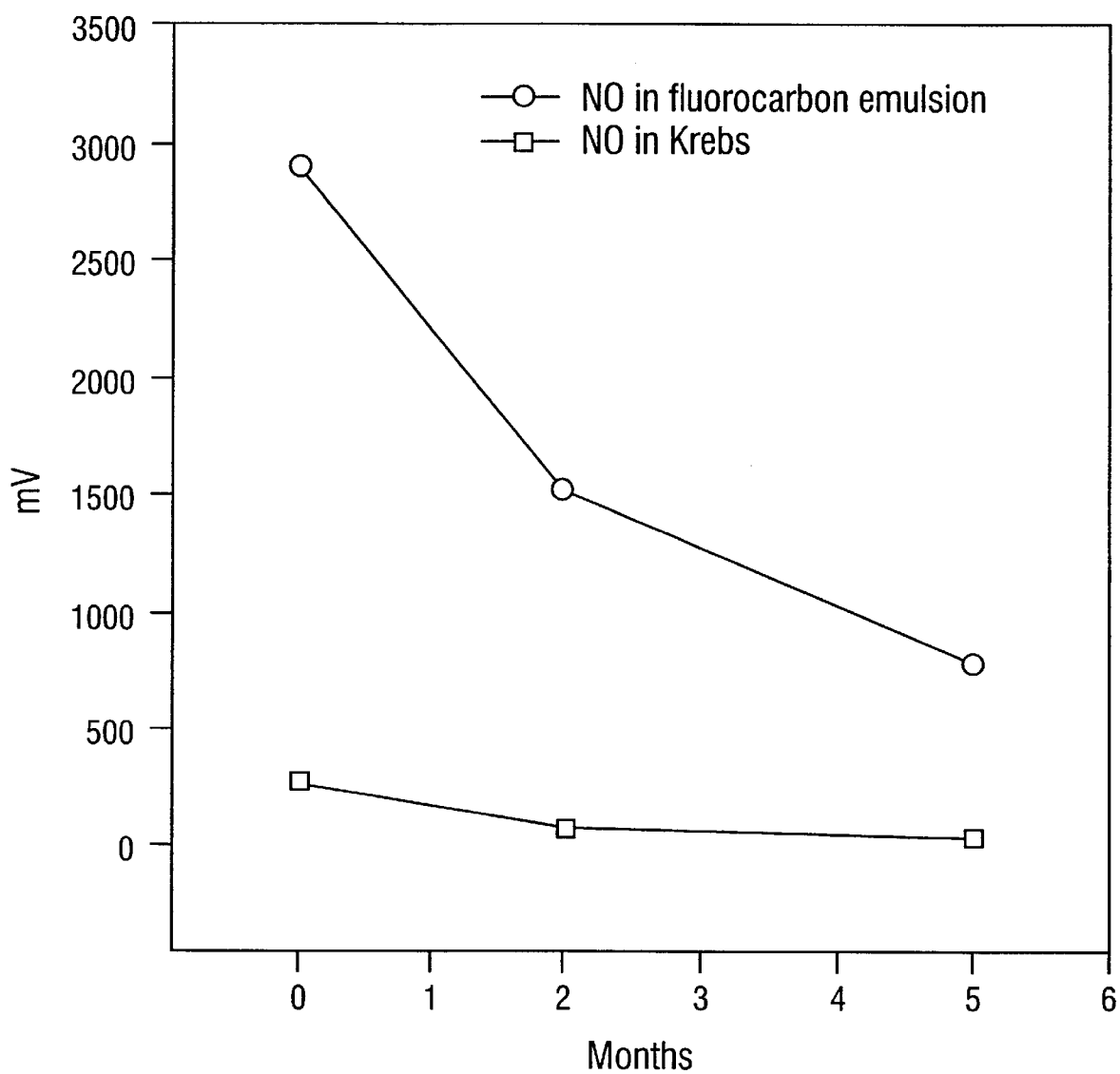
FIG. 2 presents the effect of an NO solution in the emulsion of perfluoro compound, in comparison with solutions prepared similarly in the following solvents: distilled water, 0.9% aqueous saline solution, Krebs solution, colloidal solution of poly(vinylpyrrolidone), tetrahydrofuran.

FIG. 2 presents the effect of an NO solution in the emulsion of perfluoro compound, in comparison with solutions prepared similarly in the following solvents: distilled water, 0.9% aqueous saline solution, Krebs solution, colloidal solution of poly(vinylpyrrolidone), tetrahydrofuran.

The stability of NO in Krebs' solution (a physiological solution) and the fluorocarbon emulsion. Immediately after preparing the solutions, the emulsion contains more than ten times the amount of NO as the Krebs' solution. NO in Krebs' solution disappears within a matter of about 10 minutes but NO in the emulsion is relatively stable and decreases slowly over months. FIG. 2 shows that NO dissolved in a perfluoro compound emulsion is stable for prolonged periods.

EXAMPLE 3

Effects of a NO-containing Perfluoro Compound Emulsion on Arterial Tension

Rat aortic rings, excellent ex vivo models for vascular tension control and for biological tissue sensitivity, were tested for contractile responses to agents known to have vascular effects, to perfluoro compound emulsions and to NO-containing perfluoro compound emulsions prepared as described above (argon deoxygenation followed by NO dissolution.

FIG. 3A–D shows tracings of contractions of rat aortic rings in vitro. The aorta was removed from adult female rats and suspended in physiological solution bubbled with $O_2$—$CO_2$ gas (95:5). Contractility is measured with strain gauges connected to a computer.

FIG. 3A shows control contractile response to KCl (45 mM), phenylephrine ($10^{-9}$M to $10^5$M), followed by relaxation responses to acetylcholine ($10^{-8}$M to $10^{-5}$M, known to stimulate endogenous nitric oxide release). FIG. 3B shows aortic contractile responses to Kc1, L-NAME (L-nitroarginine methyl ester), phenylephrine and to sodium nitroprusside (SNP, $10^{-9}$M to $10^{-5}$M, a known nitric oxide donor). No effect is seen following application of the deoxygenated perfluoro compound emulsion alone to aortic tissue rings (FIG. 3C) subjected to L-NAME and phenylephrine. FIG. 3D shows a typical relaxation response to application of 100 $\mu$l of a saturated preparation of nitric oxide in the emulsion.

REFERENCES

The following references are incorporated by reference in pertinent part herein for their pertinent background teachings.

Abdalla et al., "Prevention of bone mineral loss in postmenopausal women by norethisterone," *Obstet. Gynecol.*, 66:789–792, 1985.

Ahokas et al., "Enhanced endothelium-derived relaxing factor activity in pregnant spontaneously hypertensive rats," *Am. J. Obstet. Gynecol.*, 164:242, 1991.

Alam et al., "A Hypothesis for the Local Control of Osteoclast Function by CA2+, Nitric Oxide and Free Radicals," *Bioscience Reports*, 12(5):369–380, 1992. Bredt and Snyder, "Isolation of nitric oxide synthetase, a calmodulin-requiring enzyme," *Proc. Natl. Acad. Sci. USA*, 87:682–685, 1990.

Christiansen et al., "Prevention of early postmenopausal bone loss: Controlled 2-year study in 315 normal females," *Eur. J. Clin. Invest.*, 10:273–279, 1980.

Chwalisz et al., "Cervical ripening with the cytokines interleukin 8 (IL-8), interleukin 1β (IL-β) and tumor necrosis factor alpha (TNF-a) in guinea pigs," *Human Reproduct*, (in press).

Chwalisz, "Role of progesterone in the control of labor," In: Chwalisz K and Garfield RE. (eds) *Basic Mechanisms Controlling Term and Preterm Labor*, Ernst Schering Research Foundation Workshop 7, Springer Verlag, Berlin, Heidelberg, New York, London, Paris, Tokyo, Hong Kong, Barcelona, Budapest, pp. 97–163, 1993.

Chwalisz, "The use of progesterone antagonists for cervical ripening and as an adjunct to labour and delivery," *Human Reprod.*, 9(1):131–161, 1994.

Clark and Gollan, "Survival of mammals breathing organic liquids equilibrated with oxygen at atmospheric pressure," *Science*, 152:1755–1756, 1966.

Clark and Shaw, Eur. Pat. Appl. EP 231, 091 (Aug. 5, 1987), *Chem. Abstr.*, 107:242588, 1987.

Erner, U.S. Pat. No. 4,931,472, Jun. 3, 1990; *Chem. Abstr.* 1990, 113, 138569.

Furchgott and Zawkzki, "The obligatory role of endothelial cells in the relaxation of arterial smooth muscle by acetylcholine," *Nature*, 288:373–376, 1980.

Garfield and Yallampalli, "Control of myometrial contractility and labor," In: *Basic Mechanisms Controlling Term and Preterm Birth*, Ed. K. Chwalisz, RE Garfield, Springer-Verlag, New York, 1993.

Garside, "A chemiluminescent technique for the determination of nanomolar concentrations of nitrite and nitrate in sea water," *Marine Chemistry*, 11:159–167, 1982.

Geyer, "Fluorocarbon-polyol artificial blood substitute," *New Eng. J. Med.*, pp. 1077–1082, 1973.

Ignarro, "Commentary: signal transduction mechanisms involving nitric oxide," *Biochem. Pharmacol.*, 41:485–490, 1991.

Izumi et al., "Gestational changes in L-arginine-induced relaxation of pregnant rat and human myometrial smooth muscle," *Am. J Obstet. Gynecol.*, 169:1327–1337, 1993.

Kasten et al., "Potentiation of osteoclast bone-resorption activity by inhibition of nitric oxide synthase," *Proc. Natl. Acad. Sci. USA*, 91:3569–3573, 1994.

Kaufman and Thomas, PCT Intern. Appl. WO 89 10,118 (Nov. 2, 1989), *Chem. Abstr.*, 113:46356, 1990.

Lees et al., "Arrest of preterm labor and prolongation of gestation with glyceryl trinitrate, a nitric oxide donor," *Lancet*, 343:1325–1326, 1994.

Lowe, "Perfluorochemicals in medicine," *Chemistry and Industry (London)*, pp. 83–87, 1991.

Lowe, *Chemistry and Industry (London)*, 83–87, 1991.

Lowik et al, "Inducible Production of Nitric Oxide in Osteoblast-like Cells and in Fetal Mouse Bone Explants is Associated with Suppression of Osteoclatic Bone Resorption," *J Clin. Invest.*, 93:1465–1472, 1994.

MacIntyre et al, "Osteoclastic inhibition: An action of nitric oxide not mediated by cyclic GMP," *Proc. Natl. Acad. Sci. USA*, 88:2936–2940, 1991.

Mellon et al., "Reduction of biological effluents in purge and trap micro reaction vessels and detection of endothelial-derived nitric oxide by chemiluminiscence," *J. Molec. Cell Cardiol.*, 23:389–393, 1991.

Miller and Van Houtte, "Progesterone and modulation of endothelium-dependent responses in canine coronary arteries," *Am. Physiol, Soc.*, 261:R1022–R1027, 1991.

Miller et al., "Modulation of endothelium-dependent and vascular smooth muscle responses by oestrogens," *Phlebology*, 3:63–69, 1988.

Molnar and Hertlandy, "N-ω-Nitro-L-arginine, an inhibitor of nitric oxide synthesis, increases blood pressure in rats and reverses the pregnancy-induced refractoriness to vasopressor agents," *Am. J. Obstet. Gynecol.*, 166:1560–1567, 1992.

Moncada et al., "Nitric Oxide: physiology, pathophysiology and pharmacology," *Pharmacol. Rev.*, 43:109–142, 1991.

Pinto et al., "Endothelial-derived relaxing factor released by endothelial cells of human umbilical vessels and its impairment in pregnancy-induced hypertension," *Am. J Obstet. Gynecol.*, 164:507–513, 1991.

Riess and Le Blanc, "Preparation of perfluorochemical emulsions for biomedical use: principles, materials and methods," In: *Blood Substitutes: Preparation, Physiology, and Medical Applications*, Ed. K. C. Lowe, Ellis Horwood, Chichester, and VCH Publishers, pp. 94–129, 1988.

Riess and Le Blanc, "Solubility and transport phenomena in perfluorochemicals relevant to blood substitution and other biomedical applications," *Pure Appl. Chem.*, 54:2383–2406, 1982.

Riess and LeBlanc, In: *Blood Substitutes: Preparation, Physiology, and Medical Applications*, ed. K. C. Lowe, Ellis Horwood, Chichester, pp. 94–129, 1988.

Riess, "Highly fluorinated systems for oxygen transport, diagnosis and drug delivery," *Colloids and Surfaces A. Physicochem and Eng.* Aspects, 84:33–48, 1994b.

Riess, "Perfluorochemical emulsions for intravascular use," In: *Fluorine in Medicine in the 21st Century*, Eds. R. E. Banks, K. C. Lowe, Rapra Technol. Ltd., Shawbury, Paper 20, pp. 1–9, 1994c.

Riess, "The design and development of improved fluorocarbon-based products for use in medicine and biology," *Art. Cells, Blood Subs., and Immob. Biotech.*, 22:215–234, 1994a.

Roberts et al., "Preeclampsia: an endothelial cell disorder," *Am. J Obstet. Gynecol.*, 161(5):1200, 1989.

Schweighardt, Eur. Pat. Appi. EP 282,949 and 282, 948 (Sep. 21, 1988) with U.S. application Ser. No. 28,521 and 28,522 (Mar. 20, 1987), *Chem. Abstr.*, 110: 199223 and 199180, 1989.

Sloviter and Kamimoto, "Erythrocyte substitute for perfusion of brain," *Nature*, 216:458–460, 1967.

Venema et al., "Organization of the bovine gene encoding the endothelial nitric oxide synthase," *Bioch. et Biophy. Acta*, 1218:413–420, 1994.

Weiner et al., "Induction of calcium-dependent nitric oxide synthases by sex hormones," *Proc. Natl. Acad. Sci. USA*, 91:5212–5216, 1994.

Yallampalli and Garfield, "Inhibition of nitric oxide synthesis in rats during pregnancy produces signs similar to those of preeclampsia," *Am. J Obstet. Gynecol.*, 169:1316–1320, 1993.

Yallampalli et al., "An L-arginine-Nitric-oxide-cGMP system exists in the uterus and inhibits contractility during pregnancy," *Am. J. Obstet. Gynecol.*, 170:175–185, 1993b.

Yallampalli et al., "Nitric Oxide Inhibits Uterine Contractility During Pregnancy But Not During Delivery," *Endocrinol.*, 133(4):1899–1902, 1993a.

Zaidi et al., "Role of the Endothelial Cells in Osteoclast Control: New Perspectives," 14:97–102, 1993.

Those of skill in the art recognize that, once the information of the present invention is known, other and newly developed perfluorocarbon compound-containing emulsions may be equivalently substituted for those specifically disclosed herein as expressed in the following claims. Likewise, analogous and equivalent methods of preparation, administration and treatment will be apparent.

What is claimed is:

1. A composition consisting essentially of a perfluoro compound emulsion with nitric oxide dissolved therein.

2. The composition of claim 1 where the perfluoro compound is further defined as being a perfluorinated hydrocarbon, a perfluorinated heterocyclic compound or a perfluorinated hydrocarbon amine.

3. The composition of claim 1 where the perfluoro compound is perfluorinated decalin, perfluorinated adamantane, perfluorinated tributylamine, perfluorinated tripropylamine, perfluorinated N-methyl-isoquinoline, perfluorinated N-(4-methylcyclohexyl)-piperidine), perfluorinated 2-n-butyl-tetrahydrofuran, perfluorooctyl-ethane, perfluorohexyl-ethane, 1,2-bis(perfluorobutyl)-ethene or 1,2-bis(perfluorohexyl)-ethene.

4. A method for preparing a nitric oxide source suitable for in vivo administration, the method comprising preparing or obtaining an emulsion consisting essentially of a perfluoro compound having nitric oxide dissolved in said emulsion.

5. A method for treating a mammal with nitric oxide comprising administering a composition consisting essentially of a perfluoro compound emulsion and nitric oxide in a therapeutically effective amount.

6. A method for treating hypertension comprising administering a composition consisting essentially of a perfluoro compound emulsion with nitric oxide dissolved therein in a therapeutically effective amount.

7. The method of claim 5 or 6 where the administering is parenteral, topical or intracavitary.

8. The method of claim 7 where the intracavitary administration is bronchial, cervical, uteral, vaginal, oral or anal.

9. The method of claim 7 where the parenteral administration is intravascular.

10. The method of claim 5 where nitric oxide treatment is to enhance blood perfusion to a particular site and the administration is proximate to that site.

* * * * *